United States Patent [19]

Sano et al.

[11] Patent Number: 4,727,056

[45] Date of Patent: Feb. 23, 1988

[54] RECORDING MATERIAL

[75] Inventors: Shojiro Sano, Shizuoka; Ken Iwakura, Kanagawa, both of Japan

[73] Assignee: Fuji Photo Film Co., Ltd., Kanagawa, Japan

[21] Appl. No.: 849,636

[22] Filed: Apr. 9, 1986

[30] Foreign Application Priority Data

Apr. 10, 1985 [JP] Japan .................. 60-75934

[51] Int. Cl.$^4$ .................. B41M 5/16; B41M 5/18; B41M 5/22
[52] U.S. Cl. .................. 503/218; 427/150; 427/151; 503/221; 549/227
[58] Field of Search .................. 346/217, 221, 225; 427/151, 150; 549/227; 503/218

[56] References Cited

U.S. PATENT DOCUMENTS 4,390,616 6/1983 Sato et al. .................. 346/221
4,433,156 2/1984 Ishige et al. .................. 549/227
4,436,920 3/1984 Sato et al. .................. 549/227

*Primary Examiner*—Bruce H. Hess
*Attorney, Agent, or Firm*—Sughrue, Mion, Zinn, Macpeak & Seas

[57] ABSTRACT

A recording material comprising at least one electron-donating colorless dye having, in a 95% acetic acid solution, a maximum absorption at a wavelength of from 400 to 550 nm in the spectral absorption range of from 400 to 700 nm, and at least one fluoran derivative represented by formula (I)

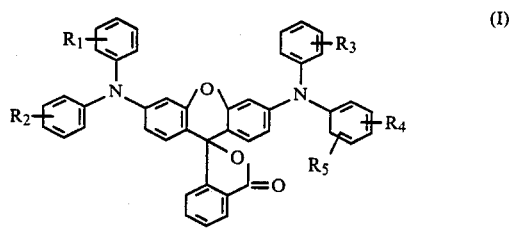

wherein $R_1$, $R_2$, $R_3$, $R_4$ and $R_5$ each represents a hydrogen atom, a lower alkyl group, a lower alkenyl group, a lower alkoxy group, nitro, amino, cyano, acylamino, dialkylamino or a halogen atom.

21 Claims, No Drawings

RECORDING MATERIAL

BACKGROUND OF THE INVENTION

The present invention relates to a recording material, and, more particularly, to a pressure-sensitive or heat-developable recording material that uses an electron-donating colorless dye and an electron-accepting compound, and which exhibits an improved color image stability.

Pressure-sensitive or heat-developable recording materials using electron-donating colorless dyes and electron-accepting compounds are disclosed in many patents such as Japanese Patent Publication Nos. 14039/1970 and 4160/1968. The essential requirements that should be satisfied by pressure-sensitive or heat-developable recording materials are: (1) satisfactory color density and sensitivity; (2) the absence of fog (i.e., coloration during storage prior to use); and (3) satisfactory fastness of a colored image. However, none of the products available today totally satisfy these requirements. With conventional recording material of the type that produces a black image, light or other environmental factors tend to cause browning or complete fading of the color image; strong need exists to eliminate this problem.

Many researchers have made studies to develop a method for producing stabilized color images. Three of the methods proposed so far are: (1) addition of a phenolic derivative such as 2,2'-methylenebis(4-methyl-6-tert-butylphenol) (see Japanese Patent Publication No. 43386/1976); (2) addition of a water-insoluble, modified (e.g., rosin-modified) phenolic resin as described in Japanese Patent Application (OPI) No. 17347/1978 (the term "OPI" used herein means "a published unexamined Japanese patent application"); and (3) addition of a terephthalic acid ester as shown in Japanese Patent Application No. 72996/1981. However, the images resulting from the recording materials prepared by these methods are still unsatifactory in terms of stability.

SUMMARY OF THE INVENTION

The principal object, therefore, of the present invention is to provide a black color-forming recording material that exhibits good color-forming properties and high color image stability, and satisfying other desired properties.

This object of the present invention can be attained by using a recording material comprising at least one electron-donating colorless dye having, in a 95% acetic acid solution, a maximum absorption at a wavelength of from 400 to 500 nm in the spectral absorption range of from 400 to 700 nm, and at least

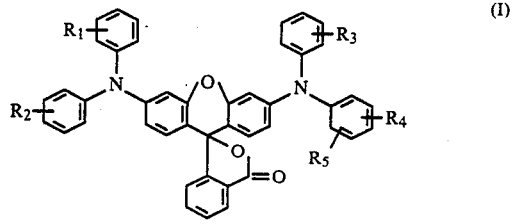

(I)

wherein $R_1$, $R_2$, $R_3$, $R_4$ and $R_5$ (which may be the same or different) each represents a hydrogen atom, a lower alkyl group, a lower alkenyl group, nitro, amino, cyano, acylamino, dialkylamino a lower alkoxy group, nitro, amino, cyano, acylamino, dialkylamino or a halogen atom.

DETAILED DESCRIPTION OF THE INVENTION

The fluoran derivative according to the present invention has proposed as described in U.S. Pat. Nos. 4,436,920 and 4,390,616 to use a diarylaminofluoran derivative as a color former in these recording materials, with which color images having remarkably excellent light-fastness can be provided.

Preferred examples of the substituents represented by $R_1$, $R_2$, $R_3$, $R_4$ and $R_5$ in formula (I) include a hydrogen atom, lower alkyl groups having from 1 to 5 carbon atoms, lower alkenyl groups having from 2 to 5 carbon atoms, lower alkoxy groups having from 1 to 5 carbon atoms, a chlorine atom, a fluorine atom, and a bromine atom. Particularly preferred examples are a hydrogen atom, a methyl group, an ethyl group, a propyl group, an isopropyl group, a butyl group, an isobutyl group, a sec-butyl group, an isopropenyl group, a methoxy group, an ethoxy group, a propyloxy group, a chlorine atom, and a fluorine atom.

Typical examples of the fluoran derivatives represented by formula (I) are set forth below.

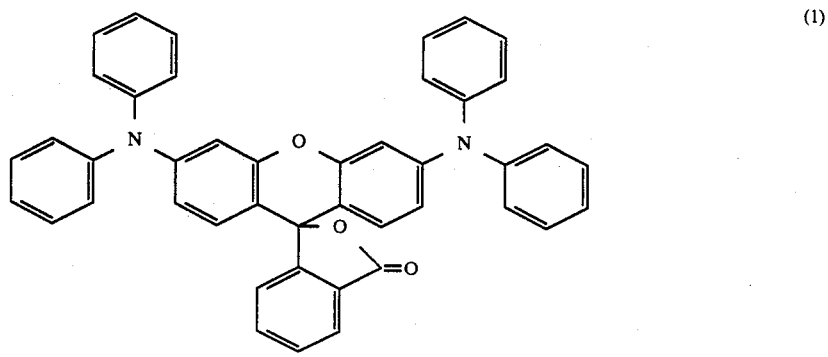

(1)

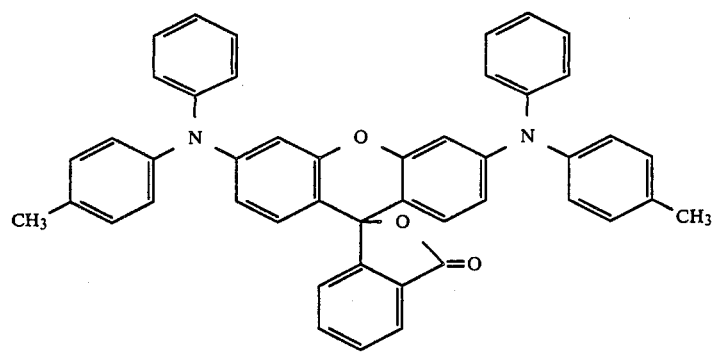
(2)
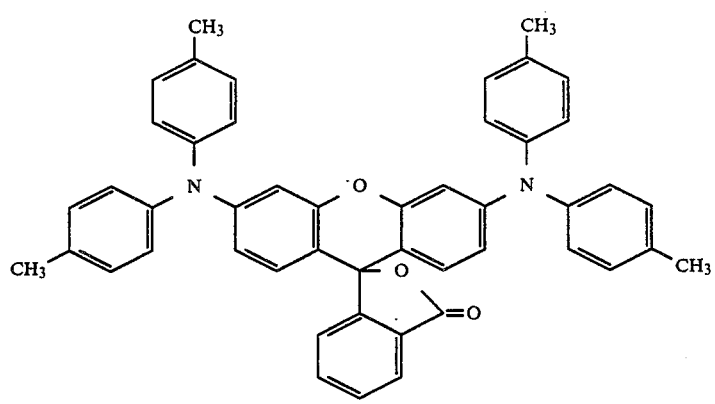
(3)
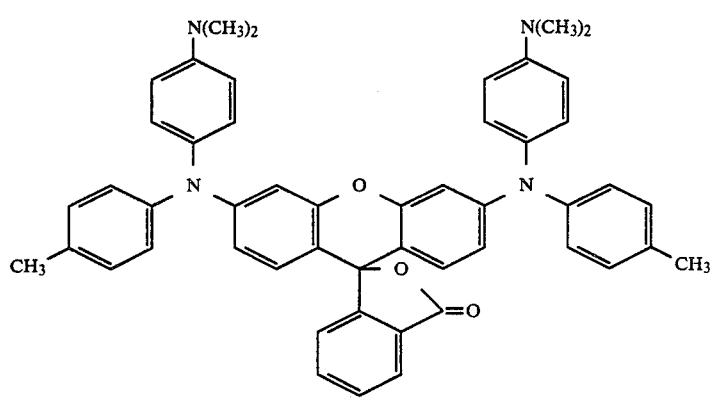
(4)
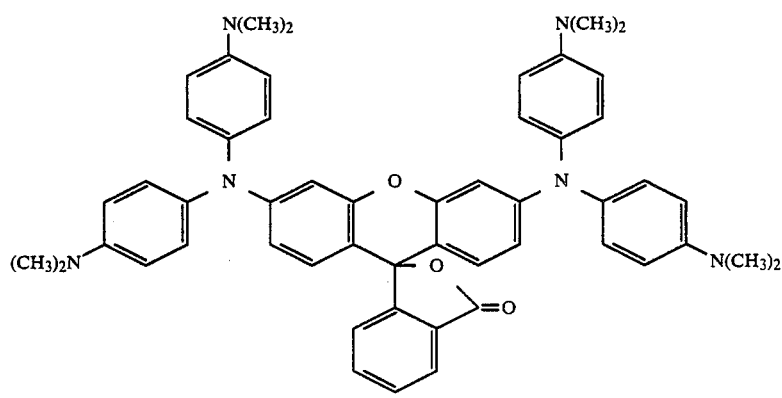
(5)

-continued
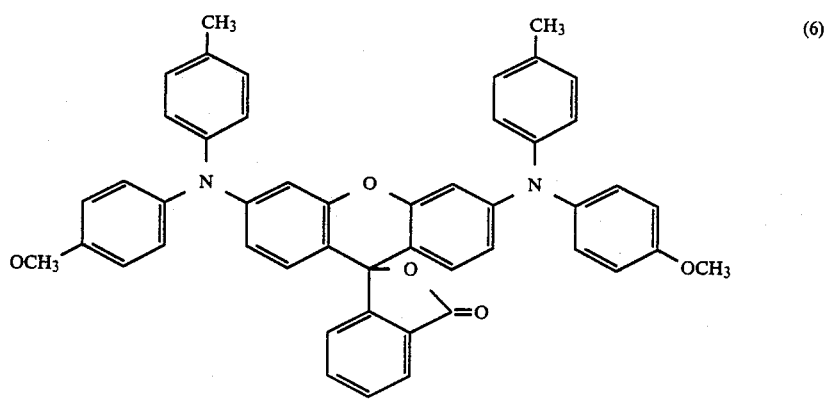 (6)
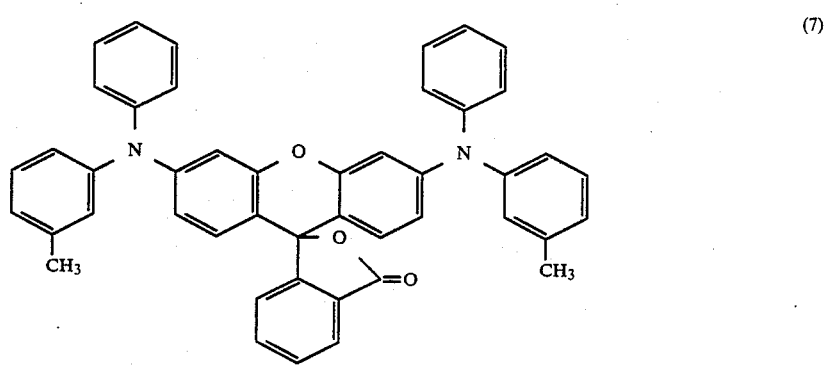 (7)
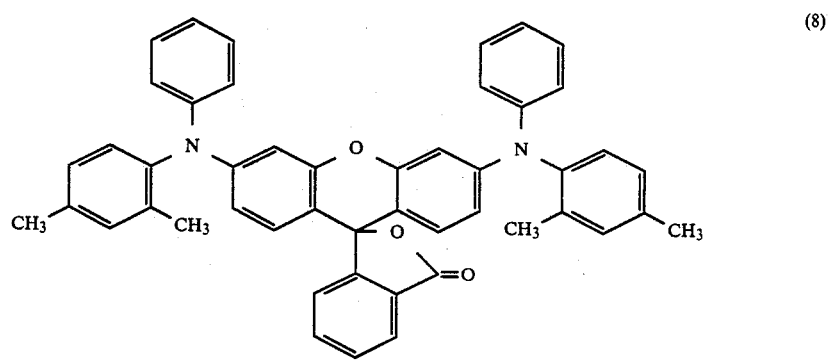 (8)
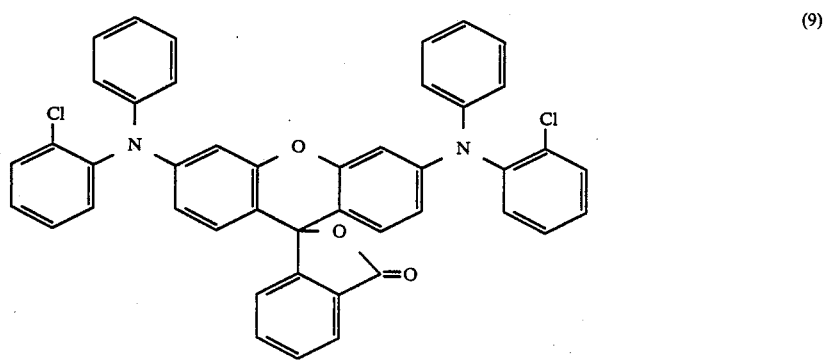 (9)

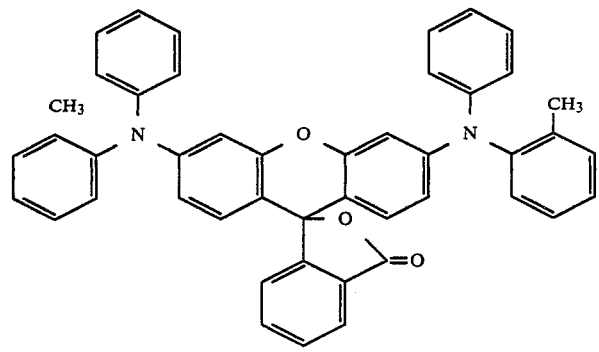
(10)
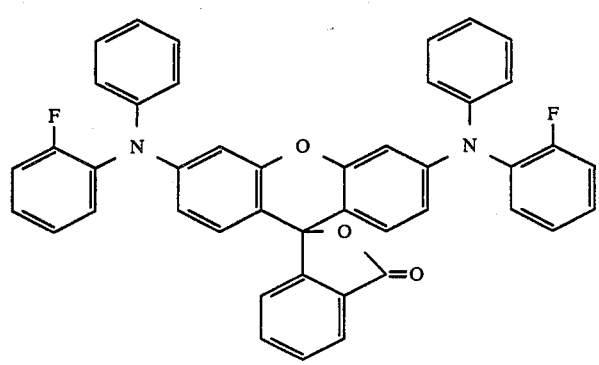
(11)
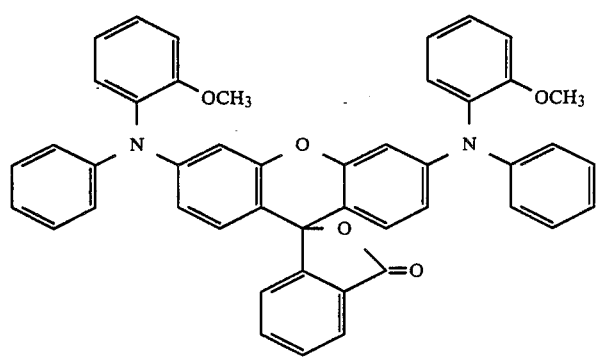
(12)
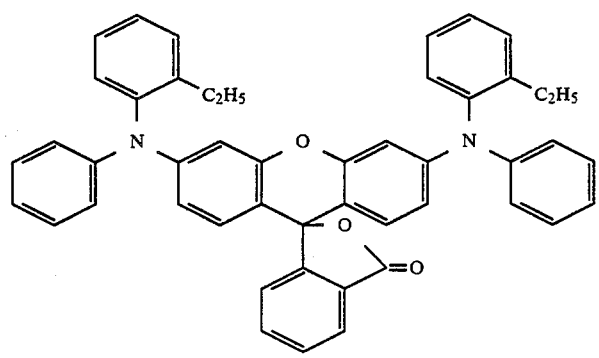
(13)

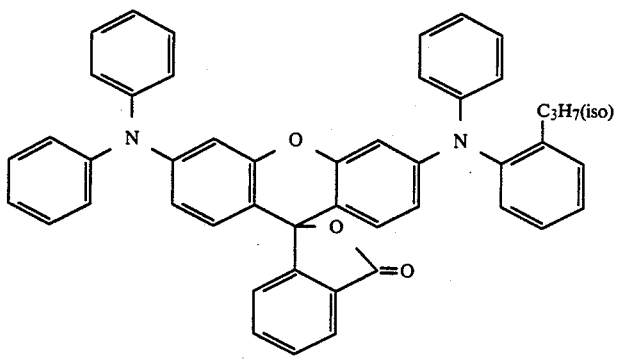
(14)

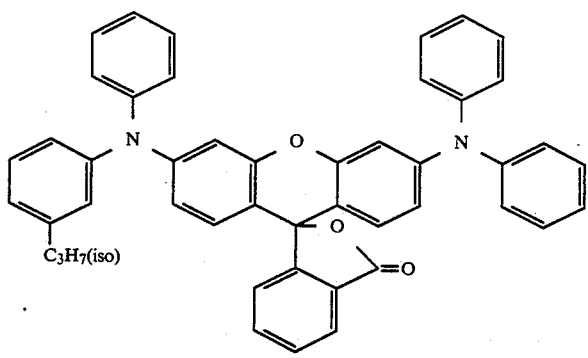
(15)

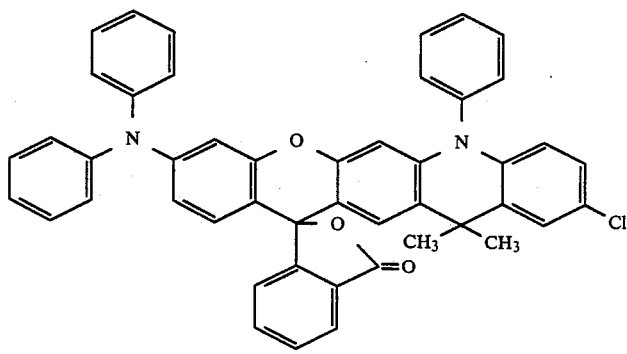
(16)

These compounds may be used individually or in admixture.

Examples of the electron-donating colorless dye that is used in the present invention and which has a maximum absorption at a wavelength of from 400 to 550 nm in the spectral absorption range of from 400 to 700 nm in a 95% acetic acid solution include fluoran compounds, heterocyclic phthalide compounds, spiropyran compounds, and pyridine compounds in order to obtain an excellent black colored image which is excellent in light fastness. In these compounds, a fluoran compound is preferred. Typical examples of such compounds are set forth below.

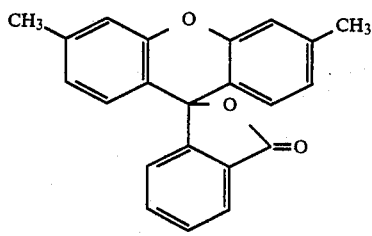
(1)

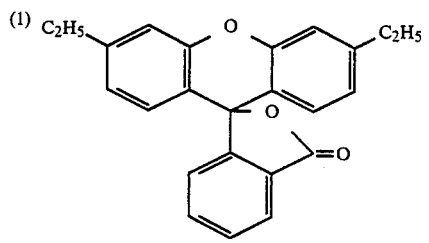
(2)

-continued
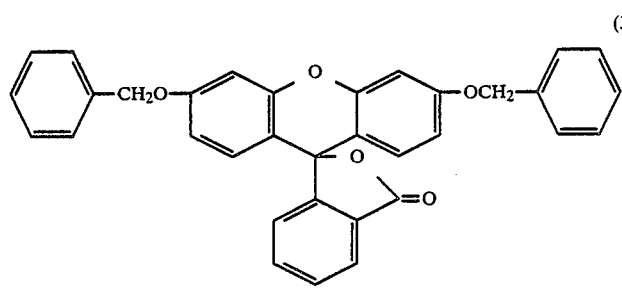 (3)
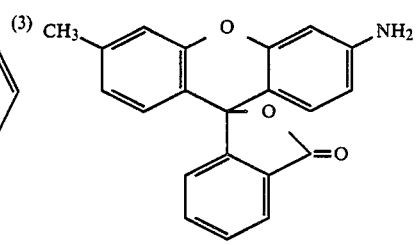 (4)
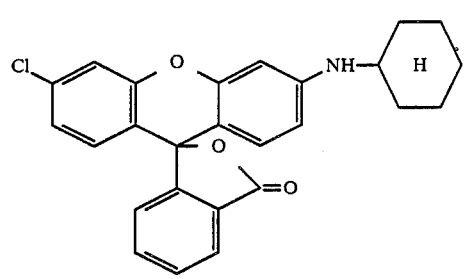 
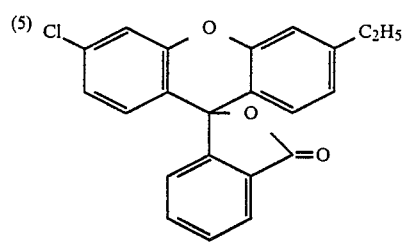 (6)
(5)
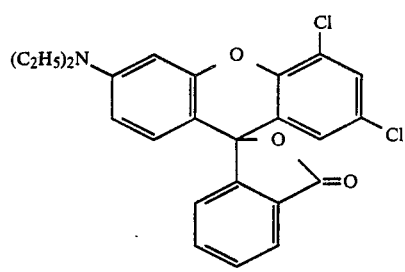 (7)
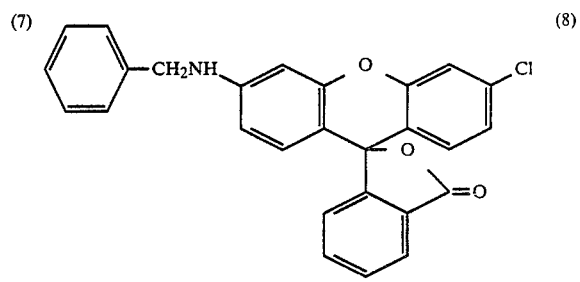 (8)
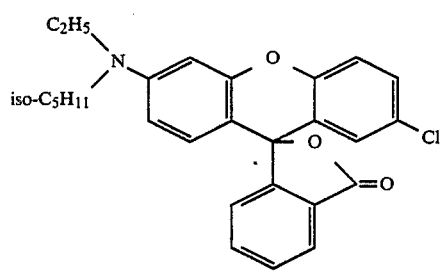 (9)
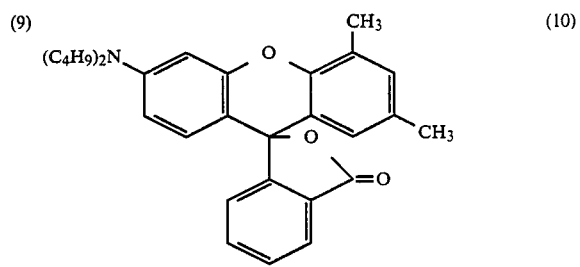 (10)
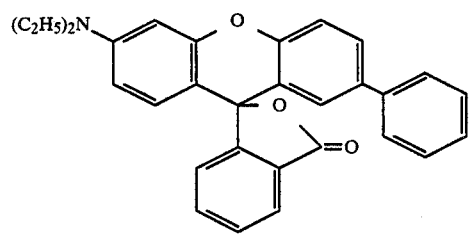 
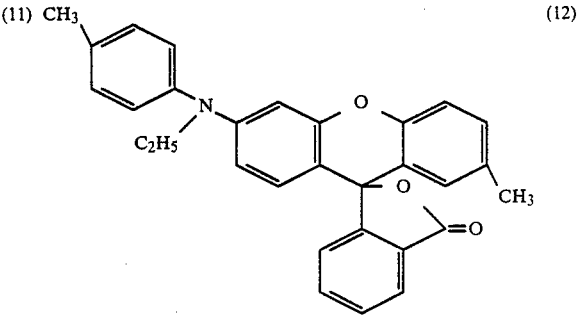 (12)
(11)

-continued
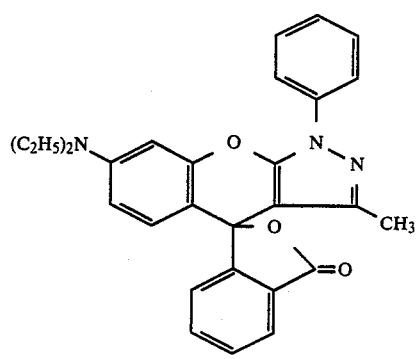
(13)
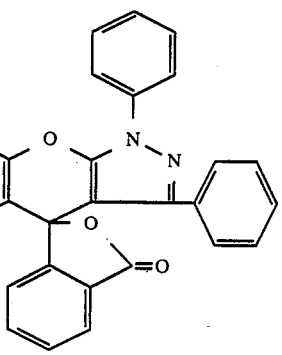
(14)
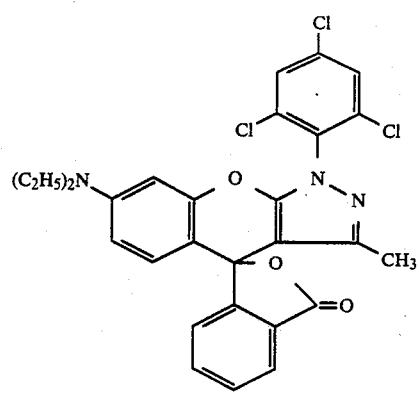
(15)
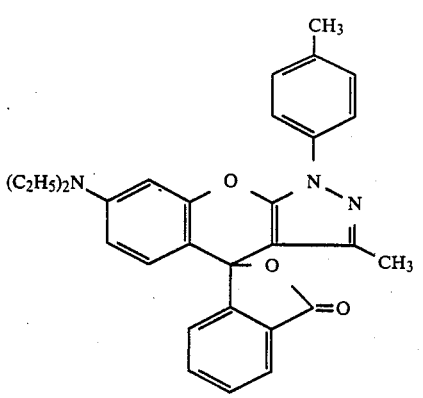
(16)
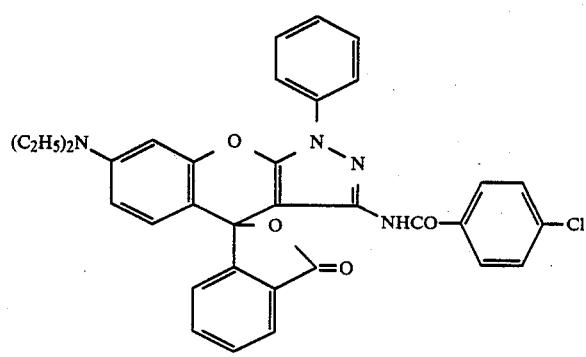
(17)
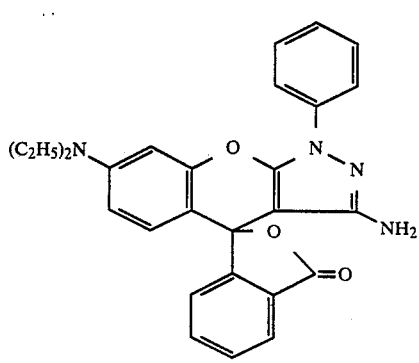
(18)
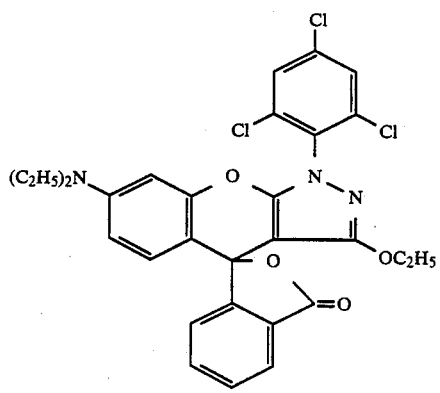
(19)
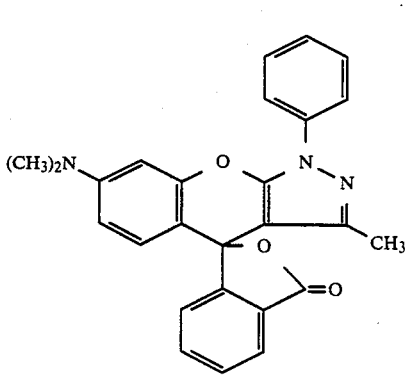
(20)

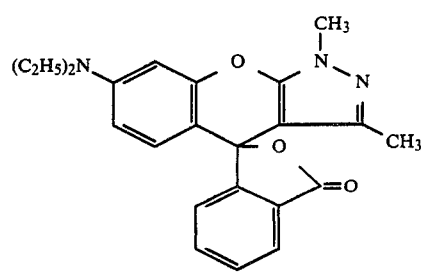
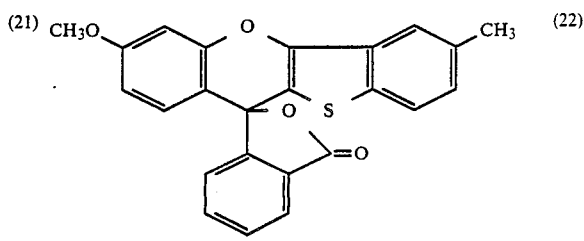
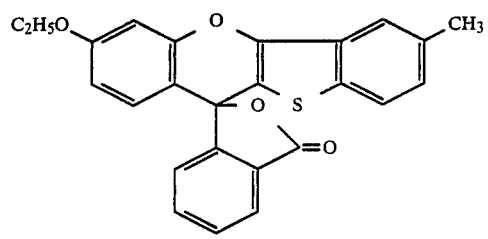
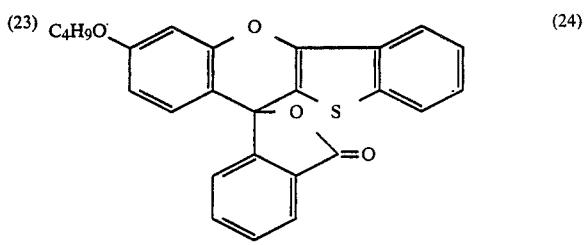
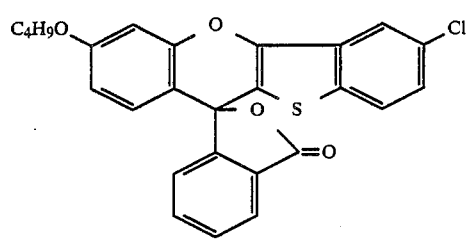
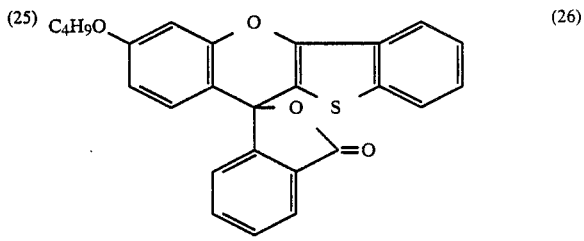
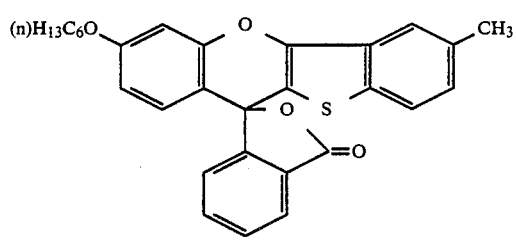
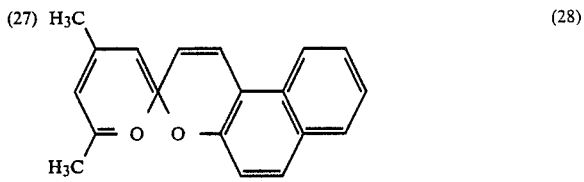
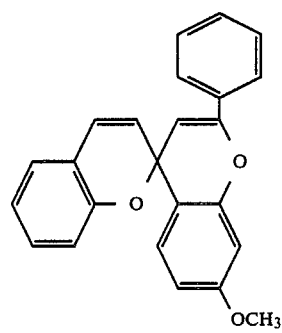
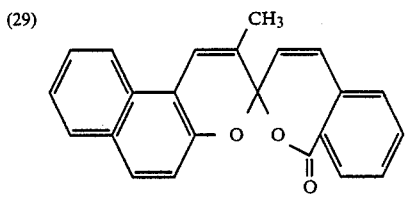
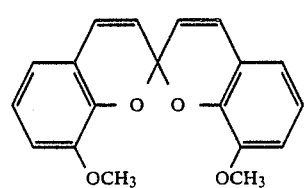
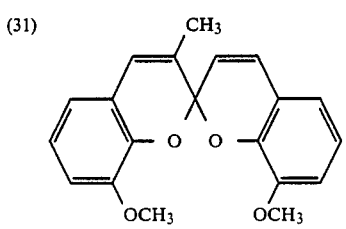

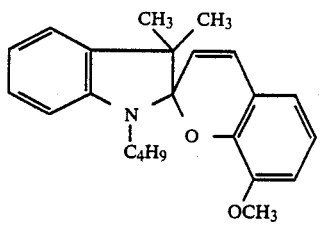

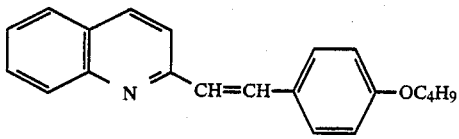

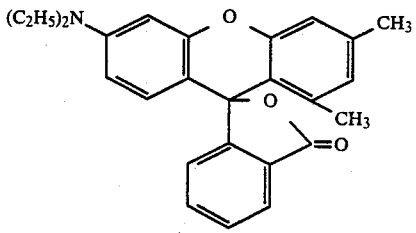

-continued

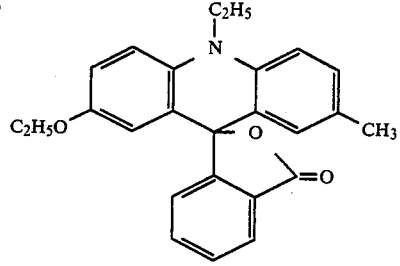

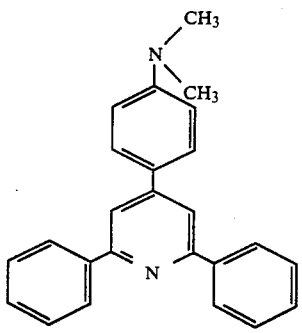

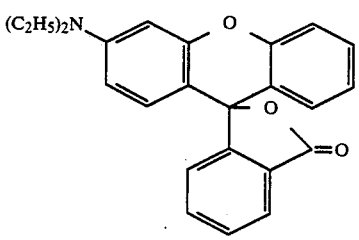

These compounds may be used either independently or in admixture.

The fluoran derivative of formula (I) and the electron-donating colorless dye having a maximum absorption at from 400 to 500 nm may be used in proportions that preferably range from 10/1 to 1/10 (on a weight basis), and more preferably from 1/1 to 1/5.

The recording material containing the fluoran derivative defined above has a satisfactory color density and the resulting colored dye is so much more stable than dyes produced from existing color formers that it will experience little change of color or fading by prolonged exposure to light, heat, or moisture. Therefore, the recording material of the present invention is particularly advantageous for the purpose of extended storage of the recorded image. The fluoran derivative itself has superior stability and exhibits nearly ideal capabilities as a recording material in that it will not be deteriorated or stained as a result of extended storage.

A heat-developable recording material containing two or more color formers is likely to fog in the background, but this problem is substantially absent from the combination of the color formers specified by the present invention.

Specified procedures for preparing the recording material of the present invention are described below.

If the recording material is a pressure-sensitive copy paper, it may assume a variety of forms as those described in prior patents such as U.S. Pat. Nos. 2,505,470, 2,505,471, 2,505,489, 2,548,366, 2,712,507, 2,730,456, 2,730,457, and 3,418,250. The most commmon form will consist of at least one pair of sheets separately containing the electron-donating colorless dyes of the present invention and an electron-accepting compound. This product may be prepared by the following method: the electron-donating colorless dyes used either independently or in combination are dissolved in solvents (synthetic oils such as alkylated naphthalene, alkylated diphenyl, alkylated diphenylmethane, alkylated diaryle-thane, and chlorinated paraffin), and the solution is dispersed in a binder or confined in microcapsules, followed by application to a support (e.g., paper, plastic sheet, or resin-coated paper) so as to prepare a color former sheet; in a separate step, electron-accepting compounds (e.g., acid clay, activated clay, phenolic resin, or a metal salt of alkyl- or aralkyl-substituted salicylic acid) taken individually or in combination are dispersed in a binder (e.g., styrene-butadiene latex or polyvinyl alcohol) and the dispersion is applied onto a base (e.g., paper, plastic sheet, or resin-coated paper) to make a color developer sheet.

The optimum amounts of the electron-donating colorless dyes and the electron-accepting compounds employed will depend upon the desired coating thickness, the form of the specific pressure-sensitive copy paper, the method of preparing microcapsules and other conditions, and may be readily determined by those skilled in the art.

Capsules may be formed by using the coacervation of hydrophilic colloid sols as described in U.S. Pat. Nos. 2,800,457 and 2,800,458 as well as by interfacial polymerization of the types described in British Pat. Nos. 867,797, 950,443, 989,264, and 1,091,076.

If the recording material of the present invention is used as a heat-developable recording material, a coating solution may be prepared by the following procedures: a binder dissolved or dispersed in a suitable solvent or dispersion medium is first prepared; then, adequately fine particles of a dye precursor containing the fluoran derivative of the present invention, a phenolic material and, optionally, a heat-fusible material are added to the binder solution or dispersion, followed by addition of an inorganic pigment such as kaolin, talc, or calcium carbonate. If desired, the coating solution may contain a suitable additive such as a paraffin wax emulsion, a latex-based binder, a sensitivity modifier, a metal soap, an antioxidant, hindered phenol, Glauber's salt, sodium chloride, a charge modifier (e.g., sorbitol), an anti-foaming agent, or a UV absorber.

The coating solution thus prepared is applied to a base such as paper, plastic sheet, or resin-coated paper and the web is dried. In preparing the coating solution, all of the necessary components may be ground in the form of a mixture; alternatively, several combinations of components may be seperately ground and dispersed before mixing.

Preferred phenolic derivatives are those having at least one phenolic hydroxyl group, and more preferred examples are those phenols which are unsubstituted at either the 2- or the 6-position, such as bis-(4-hydoxyphenyl)alkane derivatives, bis-(3-chloro-4-hydroxyphenyl)alkane derivatives, bis-(4-hydroxyphenyl)sulfone, (4-hydroxyphenyl)-(4'-alkoxyphenyl)sulfone derivatives, p-hydroxybenzoic acid ester derivatives, resorcylic acid ester derivatives, orsellinic acid ester derivatives, gallic acid ester derivatives, and salicylic acid, or alkyl- or aralkyl-substituted forms or zinc salts thereof.

Typical examples of these phenolic derivatives are listed below:
(1) 2,2-bis(4-hydroxyphenyl)propane;
(2) 1,1-bis(4-hydroxyphenyl)hexane;
(3) 1,1-bis(3-chloro-4-hydroxyphenyl)cyclohexane;
(4) 1,1-bis(3-chloro-4-hydroxyphenyl)-2-ethylbutane;
(5) benzyl p-hydroxybenzoate;
(6) zinc 3,5-di-$\alpha$-methylbenzylsalicylate;
(7) 4,4'-dihydroxy-3'-isopropyldiphenylsulfone;
(8) 1,1-bis(4-hydroxyphenyl)cyclohexane;
(9) cinnamyl resorcylate ester;
(10) $\beta$-phenetyl orsellinate;
(11) 4-N-benzylsulfamoyl phenol;
(12) $\beta$-o-chlorophenoxyethyl resorcinate;
(13) p-2,4'-dimethylbenzenesulfonyl phenol;
(14) p-methylbenzyl resorcinate ester;
(15) 2,4-dimethylphenoxyethyl resorcinate ester;
(16) $\beta,\beta'$-bis-4-hydroxyphenyl thioethyl ether;
(17) $\beta$-phenoxyethyl resorcinate ester; and
(18) $\beta,\beta'$-bis-4-hydroxyphenyl thioethyloxymethane.

Among these phenolic compounds, alkylene bisphenols, cycloalkylene bisphenols, and those having an electron attractive group are particularly useful.

Neutralized paper is particularly preferable for use as a support base in the present invention since it is comparatively insensitive to the sort of fog that may occur in a fresh or stored recording material.

A typical composition of the heat-developable recording material contains from 1 to 2 parts by weight of the electron-donating colorless dyes, from 1 to 6 parts by weight of an electron-accepting compound, up to 30 parts by weight of a heat-fusible material, up to 15 parts by weight of a pigment, from 1 to 15 parts by weight of a binder, and small amounts of appropriate additives and dispersion medium.

Generally, the amount of the electron-donating dyes to be used is from 0.01 to 0.5 $g/m^2$, preferably from 0.03 to 0.2 $g/m^2$, and the amount of the electron-accepting compounds to be used is from 0.05 to 1 $g/m^2$, preferably 0.1 to 0.5 $g/m^2$.

The electron-donating colorless dyes may be employed either independently or in combination. The most desirable dispersion medium (or solvent) is water.

Illustrative binders that may be used in the present invention include a styrene-butadiene copolymer, an alkyd resin, an acrylamide copolymer, a vinyl chloride-vinyl acetate copolymer, a styrene-maleic anhydride copolymer, synthetic rubber, gum arabic, polyvinyl alcohol, and hydroxyethyl cellulose. From the viewpoint of miscibility with the dispersion medium (solvent) used, water-soluble binders such as polyvinyl alcohol, hydroxymethyl cellulose and carboxymethyl cellulose are particularly desirable.

A heat-fusible material may be used as required and is selected from the following list: erucic acid, stearic acid, behenic acid, palmitic acid, stearylamide, behenylamide, stearic acid anilide, stearic acid toluidide, N-myristoyl-p-anisidine, N-myristoyl-p-phenetidine, 1-methoxycarbonyl-4-N-stearylcarbamoylbenzene, N-octadecylurea, N-hexadecylurea, N,N-didodecylurea, phenylcarbamoyl-oxydodecane, p-t-butylphenolphenoxy acetate, p-phenylphenol-p-chlorophenoxyacetate, 4,4'-ispropylidene bismethoxybenzene, $\beta$-phenylethyl-p-phenylphenylether, 2-p-chlorobenzyloxynaphthalene, 2-benzyloxynaphthalene, 1-benzyloxynaphthalene, 2-phenoxyacetyloxynaphthalene, diphenyl phthalate ester, phenyl-1-hydroxy-2-naphthoate ester, 2-benzoyloxynaphthalene, benzyl p-benzyloxybenzoate ester, hydroquinone acetate, 1-4-diphenoxybutane, 1-phenoxy-2-p-ethylphenoxyethane, 1,2-diphenoxyethane, and 1,4-bis-p-tolyloxybutane.

The above-listed materials are colorless and solid at ordinary temperatures and have distinct melting points in the neighborhood of from 70° to 160° C., which is the temperature range generally suitable for use in the heating of heat-developable recording materials to reproduce images.

Illustrative waxes that can be used in the present invention include paraffin wax, carnauba wax, microcrystalline wax, and polyethylene wax, as well as higher aliphatic acid amides (e.g., stearylamide and ethylene bisstearoamide) and higher aliphatic acid esters.

Polyvalent metal salts of higher aliphatic acids may be used as metal soaps and they include zinc stearate, aluminum stearate, calcium stearate, and zinc oleate.

Phenols which are substituted by an alkyl group at 2- or 6-position, or both, or derivatives of such phenols, may be used as agents for providing improved image stability. Compounds preferably for this purpose are phenols that are substituted by a branched alkyl group at 2- or 6-position or both, or derivatives thereof. Also preferred are those compounds which have two or more phenolic groups in the molecule, and those having 2 or 3 phenolic groups in the molecule are particularly preferable. Examples of such particularly preferable phenolic compounds are listed below:

bis-[3,3-bis-(4'-hydroxy-3'-tert-butylphenyl)-butanoic acido]glycol ester;
bis-[3,3-bis-(4'-hydroxy-3',4'-di-tert-butylphenyl)-butanoicacido]glycol ester;
bis-[3,3-bis-(2'-methyl-4'hydroxy-5'-tert-butylphenyl)-butanoicacido]glycol ester;
1,1,3-tris(2-methy-4-hydroxy-5-tert-butylphenyl)butane;
4,4'-thiobis(3-methyl-6-tert-butylphenol);
4,4'-thiobis(2-methyl-6-tert-butylphenol);
2,2'-thiobis(4-methyl-6-tert-butylphenol);
2,2'-methylenebis(4-methyl-6-tert-butylphenol);
2,2'-methylenebis(4-ethyl-6-tert-butylphenol);
4,4'-butylidenebis(3-methyl-6-tert-butylphenol);
4,4'-methylenebis(2,6-di-tert-butylphenol);
2-tert-butyl-4-tert-butoxyphenol;
2,2-dimethyl-4-isopropyl-7-tert-butyl-6-chronomanol;
2,2-dimethyl-6-t-butyl-5-benzofuranol; and
4[[4,6-bis(tert-butylthio)-s-triazine-2-yl]amino]2,6-di-tert-butylphenol.

The use of these hindered phenols is recommended when particularly great improvements in the keeping quality of a colored image and its resistance to particle buildup are desired.

These hindered phenol compounds may be used in amounts generally ranging from 5 to 200%, preferably from 20 to 100%, by weight based on the weight of the electron-accepting compound.

The following examples are given for the purpose of further illustrating the present invention, but are not intended as limiting.

EXAMPLE 1

(1) Preparation of a color former sheet

A hundred grams of a 4.4% aqueous solution of a partial sodium salt of poly(vinylbenzenesulfonic acid) having an average molecular weight of 500,000 and a pH of 4 was prepared. Three electron-donating colorless dyes, i.e., 2.0 g of 3,6-bis(diphenylamino)fluoran, 2.5 g of 3-cyclohexylamino-6-chlorofluoran (having a maximum absorption at 470 nm in 95% acetic acid) and 0.11 g of spiro[12H-benzo(a)xanthene-12,1'-phthalan]-9-diethylamino-3'-one (having a maximum absorption at 525 nm in 95% acetic acid), were dissolved in 100 g of diisopropylnaphthalene to prepare an oil of color former. This oil was dispersed in the previously prepared aqueous solution, thereby making an O/W (oil-in-water) emulsion comprising particles with an average size of 4.5 μm. In a separate step, 6 g of melamine, 11 g of 37% aqueous formaldehyde, and 83 g of water were agitated at 60° C. for 30 minutes to make a transparent aqueous solution of a mixture of melamine, formaldehyde, and an initial condensation product of melamine and formaldehyde. This aqueous solution was added to the previously prepared emulsion. Under agitation, the pH of the resulting mixture was adjusted to 6.0 with 20% aqueous acetic acid and heated to 65° C., where it was held for 30 minutes until microcapsules formed.

To the resulting solution, 200 g of a 20% aqueous solution of etherized starch, 47 g of starch particles (average size: 40 μm), and 10 g of talc were added. By addition of water, a solution of microcapsules with a solids content of 20% was formed.

This solution was applied onto a base of raw paper (40 g/m²) with an air knife coater to form a layer having a thickness of 5 g/m² as dry solid content, and the web was dried to make a sheet of color former.

(2) Preparation of a color developer sheet

Fifteen grams of an electron-accepting compound, zinc 3,5-bis(α-methylbenzyl)salicylate, 170 g of calcium carbonate, 20 g of zinc oxide, and 1 g of sodium hexametaphosphate were dispersed in water (200 ml) with a sand grinder. To the dispersion, 100 ml of a 10% aqueous solution of polyvinyl alcohol (99% saponification; degree of polymerization, 1,000) and 10 g of carboxy-modified SBR latex were added. To the resulting mixture, water was added to give a solids content of 20%. The coating solution thus prepared was applied to a base of raw paper and the web was dried to make a sheet of color developer.

The two sheets were superposed on each other and, upon application of pressure or impact, a black-impressed image formed almost instantly. The image had a high density and exhibited superior resistance to light and heat.

EXAMPLE 2

A sheet of color former was prepared as in Example 1 except that the electron-donating colorless dyes were changed to 1.5 g of 3,6-bis(diphenylamino)fluoran, 2.8 g of spiro[chromeno[2,3-C]pyrazol-4,1'(3'H)-isobenzofuran]-7-diethylamino-3-methyl-1-p-tolyl-3'-one (having a maximum absorption at 503 nm in 95% acetic acid) and 1.5 g of 2,6-diphenyl-4-p-diethylaminophenyl pyridine (having a maximum absorption at 470 nm in 95% acetic acid). The color former sheet was superposed on a sheet of color developer that was prepared as in Example 1. Upon application of pressure, a black-impressed image formed in the assembly. The image had a high density and exhibited superior resistance to light and heat.

EXAMPLE 3

A sheet of color former was prepared as in Example 1 except that the electron-donating colorless dyes were changed to 2.0 g of 3,6-bisdiphenylaminofluoran, 2.6 g of 3-cyclohexylamino-6-chlorofluoran, and 0.1 g of 1,3-dimethyl-6-diethylaminofluoran (having a maximum absorption at 495 nm in 95% acetic acid). The color former sheet was superposed on a sheet of color developer that was prepared as in Example 1. Upon application of pressure, a black-impressed image formed in the assembly. The image had a high density and exhibited superior resistance to light and heat.

EXAMPLE 4

A sheet of color former was prepared as in Example 1 except that the electron-donating colorless dyes were changed to 1 g of 3,6-bis(diphenylamino)fluoran, 0.5 g of 3-cyclohexylamino-6-chlorofluoran, 0.25 g of spiro[12H-benzo(a)xanthene-12,1'-phthalan]-9-diethylamino-3'-one, 1.5 g of 2-benzylamino-6-diethylaminofluoran and 1.5 g of 2-anilino-3-methyl-6-N-ethyl-N-isoamylaminofluoran. The color former sheet was superposed on a sheet of color developer that was prepared as in Example 1. Upon application of pressure, a black-impressed image formed in the assembly. The image had a high density and exhibited superior resistance to light and heet.

EXAMPLE 5

A sheet of color former was prepared as in Example 1 except that the electron-donating colorless dyes were changed to 0.35 g of 3,6-bis(diphenylamino)fluoran, 0.25 g of spiro[12H-benzo(a)xanthene-12,1'-phthalan]-9-diethylamino)-3'-one and 4.4 g of 2-anilino-3-chloro-6-diethylaminofluoran. The color former sheet was superposed on a sheet of color developer that was prepared as in Example 1. Upon application of pressure, a black-impressed image formed in the assembly. The image had a high density and exhibited superior resistance to light and heet.

EXAMPLE 6

A sheet of color former was prepared as in Example 1 except that the electron-donating colorless dyes were changed to 2.0 g of 3,6-bis-diphenylaminofluoran, 2.5 g of 3-cyclohexylamino-6-chlorofluoran and 0.8 g of 3-(4-diethylamino-2-octyloxyphenyl)-3-(1-ethyl-2-methylindol-3-yl)azaphthalide.

On the other hand, a sheet of color developer was prepared as follows: 100 parts of terra abla was dispersed into 400 parts of 0.5% aqueous sodium hydroxide, followed by adding 20 parts of polymer latex (styrene-butadiene) as a solid and 40 parts of 100 wt% aqueous starch solution to obtain color developing coating solution after sufficiently mixing under agitation. The coating solution, thus formed, was applied on one side of paper (40 g/m²) to form a layer having a thickness of 5.0 g/m² as dry solid. The color former sheet was superposed on a sheet of color developer that was prepared as in Example 1. Upon application of pressure, a black-impressed image formed in the assembly. The image had a high density and exhibited superior resistance to light and heet.

EXAMPLE 7

Two grams of 3,6-bisdiphenylaminofluoran, 3.0 g of 3-cyclohexylamino-6-chlorofluoran, and 50 ml of a 5% aqueous polyvinyl alcohol solution were treated in a horizontal sand mill to make a dispersion comprising particles with an average size of 1.6 μm. Ten grams of bisphenol A, 10 g of β-naphtholbenzyl ether, 20 g of kaolin, and 100 ml of a 5% aqueous polyvinyl alcohol solution were also treated in a horizontal sand mill to make a dispersion comprising particles with an average size of 1.5 μm. The two dispersions were thoroughly mixed, and 5 g of a 50% dispersion of paraffin wax emulsion and 8 g of stearylanisidide were added to the mixture. The so-prepared coating solution was applied to a base of raw paper (50 g/m²) to form a layer in a thickness of 5 g/m² (on a solids basis), and the web was dried. The coated paper was heated in a facsimile with a thermal energy of 40 mJ/mm², thereby producing a black-impressed image. This image was very stable; its light-fastness was so great that it could be exposed under a UV lamp or a xenon lamp for 1 hour, with little change occurring in its hue and density.

EXAMPLE 8

A heat-developable recording paper was prepared as in Example 3 except that the electron-donating colorless dyes were changed to 2.0 g of 3,6-bis-(N-o-tolylanilino)fluoran, 0.5 g of 3-diethylamino-7-phenylfluoran (having a maximum absorption at 502 nm in 95% acetic acid), and 3.0 g of 2,6-diphenyl-4-p-diethylaminophenylpyridine. When the paper was heated in a facsimile with a thermal energy of 40 mJ/mm², a black-impressed image formed. This image had a high density and exhibited superior resistance to light and heat.

While the invention has been described in detail and with reference to specific embodiments thereof, it will be apparent to one skilled in the art that various changes and modifications can be made therein without departing from the spirit and scope thereof.

What is claimed is:

1. A recording material comprising a support having provided thereon a mixture comprising at least one electron-donating colorless dye having, in a 95% acetic acid solution, a maximum absorption at a wavelength of from 400 to 550 nm in the spectral absorption range of from 400 to 700 nm, and at least one fluoran derivative represented by the formula (I)

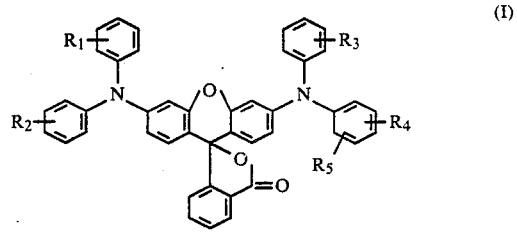

wherein $R_1$, $R_2$, $R_3$, $R_4$ and $R_5$ each represents a hydrogen atom, a lower alkyl group, a lower alkenyl group, a lower alkoxy group, nitro, amino, cyano, acylamino, dialkylamino or a halogen atom.

2. A recording material as in claim 1, wherein $R_1$, $R_2$, $R_3$, $R_4$, and $R_5$ each represents a hydrogen atom, a lower alkyl group having from 1 to 5 carbon atoms, a lower alkenyl group having from 2 to 5 carbon atoms, a lower alkoxy group having from 1 to 5 carbon atoms, a chlorine atom, a fluorine atom, or a bromine atom.

3. A recording material as in claim 2, wherein the weight ratio of the fluoran derivative of formula (I) to the electron-donating colorless dye is from 10/1 to 1/10.

4. A recording material as in claim 2, wherein the weight ratio of the fluoran derivative of formula (I) to the electron-denoting colorless dye is from 1/1 to 1/5.

5. A recording material as in claim 1, wherein $R_1$, $R_2$, $R_3$, $R_4$, and $R_5$ each represents a hydrogen atom, a methyl group, an ethyl group, a propyl group, an isopropyl group, a butyl group, an isobutyl group, a sec-butyl group, an isopropenyl group, a methoxy group, an ethoxy group, a propyloxy group, a chlorine atom, or a fluorine atom.

6. A recording material as in claim 5, wherein the weight ratio of the fluoran derivative of formula (I) to the electron-donating colorless dye is from 10/1 to 1/10.

7. A recording material as in claim 5, wherein the weight ratio of the fluoran derivative of formula (I) to the electron-donating colorless dye is from 1/1 to 1/5.

8. A recording material as in claim 1, wherein the electron-donating colorless dye is selected from fluoran compounds, heterocyclic phthalide compounds, sipropyran compounds and pyridine compounds 9. A recording material as in claim 1, wherein the electron-donating colorless dye is fluoran compounds.

10. A recording material as in claim 1, wherein the weight ratio of the fluoran derivative of formula (I) to the electron-donating colorless dye is from 10/1 to 1/10.

11. A recording material as in claim 1, wherein the weight ratio of the fluoran derivative of formula (I) to the electron-donating colorless dye is from 1/1 to 1/5.

12. A recording material as claimed in claim 1 having a light resistance of 0.9 or more in both the microcapsule layer and the color dye as calculated according to the following equation $$\text{Light Resistance} = \frac{\text{Color density } D \text{ after being exposed with Xenon lamp}}{\text{Fresh color density } D_0}$$

wherein the spectral absorption curve is measured within the range of 380 to 780 nm to obtain an absorption maximum a fresh color density ($D_0$) at the absorption maximum and wherein D is measured after exposure to Xenon lamp for 24 hours.

13. A heat-developable recording material comprising at least one electron-donating colorless dye having, in a 95% acetic acid solution, a maximum absorption at a wavelength of from 400 to 550 nm in the spectral absorption range of from 400 to 700 nm, and at least one fluoran derivative represented by formula (I)

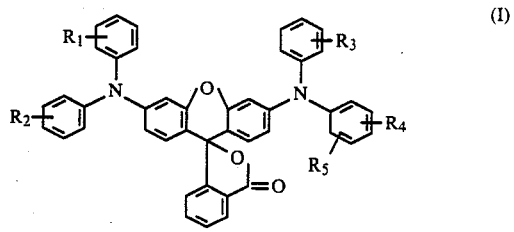

wherein $R_1$, $R_2$, $R_3$, $R_4$, and $R_5$ each represents a hydrogen atom, a lower alkyl group, a lower alkenyl group, a lower alkoxy group, or a halogen atom.

14. A heat-developable recording material as in claim 13, wherein the electron-donating colorless dye is selected from fluoran compounds, heterocyclic phthalide compounds, sipropyran compounds and pyridine compounds.

15. A heat-developable recording material as in claim 13, wherein the electron-donating colorless dye is fluoran compounds.

16. A heat-developable recording material as in claim 13, comprising from 1 to 2 parts by weight of said fluoran derivative represented by formula (I), from 1 to 6 parts by weight of said electron-donating colorless dye, up to 30 parts by weight of a heat-fusible material, up to 15 parts by weight of a pigment, and from 1 to 15 parts by weight of a binder.

17. A heat-developable recording material as in claim 13, wherein $R_1$, $R_2$, $R_3$, $R_4$, and $R_5$ each represents a hydrogen atom, a lower alkyl group having from 1 to 5 carbon atoms, a lower alkenyl group having from 2 to 5 carbon atoms, a lower alkoxy group having from 1 to 5 carbon atoms, a chlorine atom, a fluorine atom, or a bromine atom.

18. A heat-developable recording material as in claim 13, wherein $R_1$, $R_2$, $R_3$, $R_4$, and $R_5$ each represents a hydrogen atom, a methyl group, an ethyl group, a propyl group, an isopropyl group, a butyl group, an isobutyl group, a sec-butyl group, an isopropenyl group, a methoxy group, an ethoxy group, a propyloxy group, a chlorine atom, or a fluorine atom.

19. A heat-developable recording material as in claim 13, wherein the weight ratio of the fluoran derivative of formula (I) to the electron-donating colorless dye is from 1/1 to 1/5.

20. A heat-developable recording material as in claim 13, wherein the weight ratio of the fluoran derivative of formula (I) to the electron-denoting colorless dye is from 1/1 to 1/5.

21. A heat-developable recording material as in claim 13, wherein the weight ratio of the fluoran derivative of formula (I) to the electron-donating colorless dye is from 1/1 to 1/5.

* * * * *